(12) United States Patent
Hitchcock et al.

(10) Patent No.: US 10,130,729 B2
(45) Date of Patent: *Nov. 20, 2018

(54) SCENTED ODOR REDUCING COMPOSITION

(71) Applicant: Wizard Labs, LLC, Jamestown, NC (US)

(72) Inventors: Wiley William Hitchcock, Greensboro, NC (US); James Michael Puckett, High Point, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/009,992

(22) Filed: Jun. 15, 2018

(65) Prior Publication Data

US 2018/0289848 A1    Oct. 11, 2018

Related U.S. Application Data

(63) Continuation of application No. 15/869,191, filed on Jan. 12, 2018, now Pat. No. 10,022,465.

(60) Provisional application No. 62/445,510, filed on Jan. 12, 2017.

(51) Int. Cl.
*A61L 9/012* (2006.01)
*A61L 9/14* (2006.01)
*A61Q 13/00* (2006.01)
*A61K 8/19* (2006.01)
*A61K 8/92* (2006.01)
*A61K 8/34* (2006.01)
*A61K 8/04* (2006.01)

(52) U.S. Cl.
CPC .............. *A61L 9/012* (2013.01); *A61K 8/044* (2013.01); *A61K 8/19* (2013.01); *A61K 8/34* (2013.01); *A61K 8/922* (2013.01); *A61L 9/14* (2013.01); *A61Q 13/00* (2013.01); *A61K 2800/413* (2013.01)

(58) Field of Classification Search
CPC ........... A61L 9/012; A61L 9/14; A61Q 13/00; A61K 8/19; A61K 8/922; A61K 8/34; A61K 8/044; A61K 2800/413
See application file for complete search history.

(56) References Cited

U.S. PATENT DOCUMENTS

2014/0066872 A1    3/2014  Baer et al.

*Primary Examiner* — Trevor Love
(74) *Attorney, Agent, or Firm* — Kilpatrick Townsend & Stockton LLP

(57) ABSTRACT

An odor reducing composition comprising a scent and silver nanoparticles is disclosed, together with methods of making and using the same, and methods for reducing an odor.

19 Claims, 1 Drawing Sheet

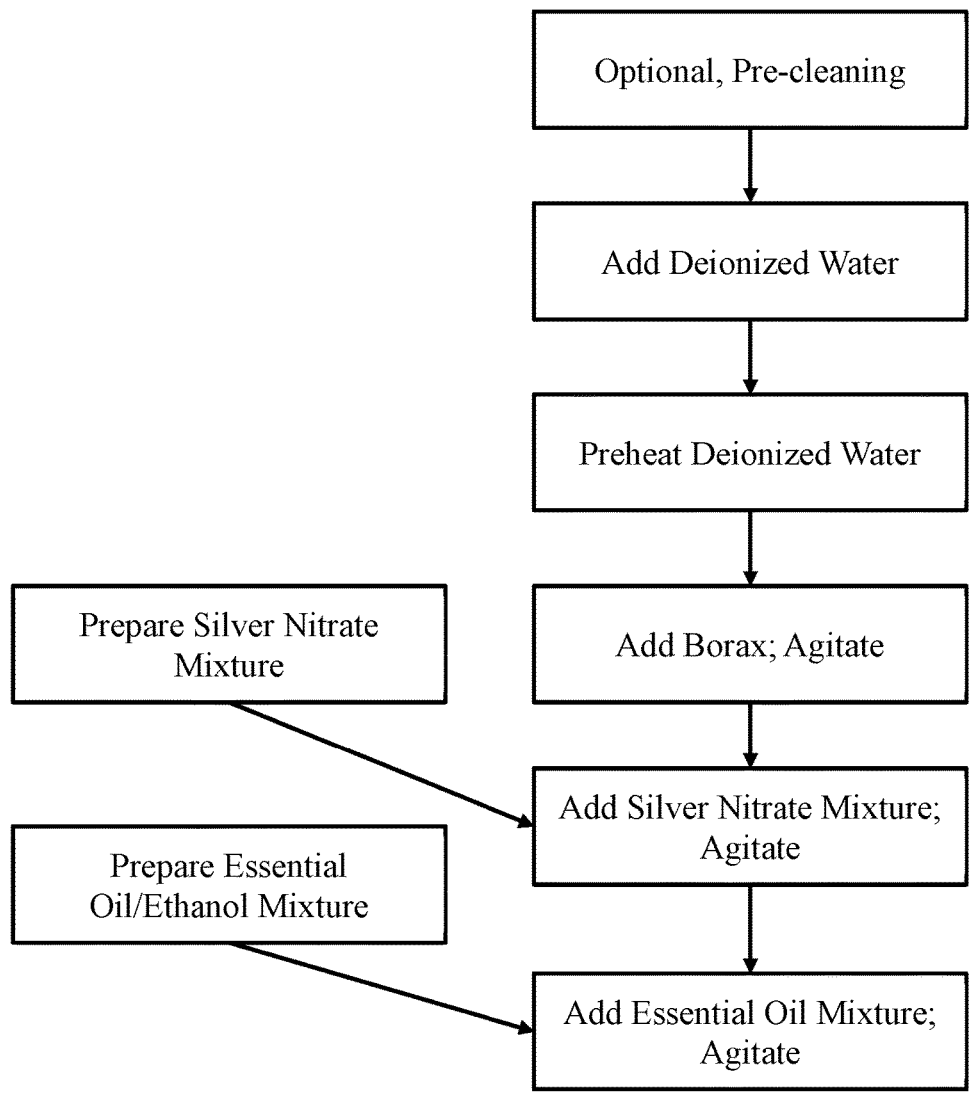

SCENTED ODOR REDUCING COMPOSITION

CROSS-REFERENCE TO RELATED APPLICATIONS

This application is a continuation of U.S. patent application Ser. No. 15/869,191, filed on Jan. 12, 2018, which claims priority to U.S. Provisional Patent Application Ser. No. 62/445,510, filed on Jan. 12, 2017, both of which are hereby incorporated by reference as though fully set forth herein.

FIELD

Described herein are compositions, methods for producing compositions and methods of using compositions. In embodiments, the compositions comprise a scent and minimize other odors. Also disclosed herein are methods for reducing an odor.

BACKGROUND

It is often advantageous and/or desirable to minimize odors in the environment, on an article and/or emanating from a human or animal. For example, pets can generate unpleasant odors in a home and a homeowner may desire to minimize the odors. There are also situations, for example, photography, hunting, surveillance and the like, where it may be advantageous for a person, and/or accompanying animal, to minimize their odors, including body odor and scents on clothing/fabric, so as not to be scentable.

SUMMARY

Described herein are compositions comprising a scent and silver nanoparticles. In an embodiment, a composition comprises: a silver nanoparticle, disodium tetraborate decahydrate (borax), a scented essential oil and deionized water. In an embodiment, a silver nanoparticle comprises uncomplexed elemental silver. In an embodiment, a composition further comprises anhydrous ethanol. In an embodiment a composition comprises a colloidal suspension comprising a plurality of silver nanoparticles.

Embodiments of compositions of the present invention may be advantageous in minimizing odor and/or eliminating the source of an odor. As used herein minimizing refers to making the odor less detectable, e.g. scentable, by a human and/or animal. In embodiments, a composition of the present invention may make an odor undetectable and therefore be said to "eliminate" the odor. In embodiments an odor refers to something other than the scent incorporated into the composition.

Embodiments of a composition of the present invention may be made by a variety of means, including by means of a method of the present invention. In an embodiment the present invention provides a method comprising: creating a colloidal suspension of silver nanoparticles and introducing a scented oil. In an embodiment, creating a colloidal suspension of silver nanoparticles comprises combining deionized water, silver nitrate and disodium tetraborate decahydrate. In an embodiment the method may further comprise combining a scented oil and ethanol and introducing the combined composition. In an embodiment, combining may further comprise mixing or agitating the resulting composition.

A composition of the present invention may be introduced to the environment, or applied to a surface in a variety of manners. In an embodiment, a method of the present invention for using a composition of the present invention comprises: introducing the composition to an environment. In embodiments, the composition may be introduced in liquid, aerosol, powder, or any other forms. In an embodiment, the composition may be introduced in a manner that allows the composition to disperse within the environment.

In another embodiment, a method of the present invention for using a composition of the present invention comprises: applying the composition to a surface. In an embodiment, the surface may comprise a portion of a human or an animal, for example the skin. In an embodiment the surface may comprise a portion of an article of manufacture, for example including, but not limited to, clothing, floor coverings, walls, counter-tops, trash bins, waste receptacles, bathroom fixtures, sinks, furniture and the like. In an embodiment, the surface may comprise the source of the odor, for example including, but not limited to, an animal, a human, a vegetable, a fruit, garbage and the like.

The present invention further provides methods for minimizing an odor. In an embodiment, a method for minimizing an odor comprises a method for using a composition of the present invention. In an embodiment, a method for minimizing an odor comprises introducing a composition of the present invention into an environment. In embodiments, the composition may be introduced in liquid, aerosol, powder or any other forms. In an embodiment, the composition may be introduced in a manner that allows the composition to disperse within the environment.

BRIEF DESCRIPTION OF THE DRAWINGS

The invention may be further understood by reference to the following non-limiting FIGURE.

FIG. 1 is a flow diagram of the method for making a scented odor reducing composition.

DETAILED DESCRIPTION OF THE INVENTION

Embodiments of the present invention include a scented odor reducing composition, methods of producing the same, methods for using the same, and methods for minimizing odors. Unlike other compositions that only mask an odor, the composition described herein may eliminate the source of the odor itself.

The invention may be embodied in a variety of ways. In certain embodiments, a scented odor reducing composition may comprise:
  0.0008 to 0.08 wt. % silver nanoparticles,
  0.18 to 7 wt. % disodium tetraborate decahydrate (borax),
  up to 5 wt. % anhydrous ethanol,
  up to 0.2 wt. % scented essential oil,
  and the remainder deionized water.

In some embodiments, the composition may comprise about 0.005 to 0.01 wt. % silver nanoparticles, 0.5 to 2 wt. % disodium tetraborate decahydrate, up to 4 wt. % anhydrous ethanol, up to 0.2 wt. % scented essential oil, and the remainder deionized water.

In some embodiments, the composition may be made with a scented essential oil capable of forming a micro-emulsion in the composition. For example, in one embodiment, the scented essential oil was Green Tea Oil, which resulted in a Green Tea scented composition. In other embodiments, the scented essential oil may be hydrophobic. Not intending to be bound by theory, a water-soluble or hydrophilic scented essential oil may bind with the silver particles, which thereby may reduce the effectiveness of the composition to eliminate odor as well as negatively impact the stability of the composition. In some embodiments, the scented essential oil may be ethanol-soluble, which may provide for improved stability of the composition.

In some embodiments, the composition may be alkaline and may have a pH greater than 8. In certain embodiments, the composition may have a pH between 9 and 10. Further, in some embodiments, an alkaline cleaner such as Enforce LP™ may be used to pre-clean equipment used to make the scented odor reducing composition.

In the present invention, the silver cations from the silver nitrate convert into silver nanoparticles when dissolved in the composition. These silver nanoparticles may function as a deodorizing and antimicrobial agent that inhibit microbial growth and bind to odors. In some embodiments, the composition comprises silver nanoparticles dispersed in a colloidal suspension at a separation distance of 10 to 100 nanometers. Furthermore, in the present invention, the disodium tetraborate decahydrate, $(Na_2B_4O_7 \cdot 10H_2O)$, commonly known as borax, may function as a deodorizing agent. Borax also serves as an efficient reagent to generate the silver nanoparticles. In the present invention, Borax may be provided in excess, with silver nitrate as the limiting reagent. The reaction of the silver nitrate and borax is provided in Equation 1.

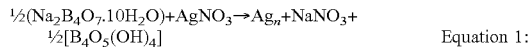

$$\tfrac{1}{2}(Na_2B_4O_7 \cdot 10H_2O) + AgNO_3 \rightarrow Ag_n + NaNO_3 + \tfrac{1}{2}[B_4O_5(OH)_4] \quad \text{Equation 1:}$$

The excess borax in the composition may serve as a weak buffer that helps stabilize the silver nanoparticles in suspension. The borax remaining in composition may function as deodorizing agent that binds and eliminates odors.

Odor reduction compositions that comprise a scent along with the antimicrobial properties of silver nanoparticles and borax are not currently available. The stability of a composition combining silver nanoparticles and borax has been shown difficult to achieve. The challenge of incorporating a scent into said composition and maintaining the long-term stability and activity may explain the lack of a scented odor reducing composition that contains silver nanoparticles and borax. A scented composition could provide efficient odor minimization while also providing a desirable odor in the targeted area. Therefore, an odor reducing composition that utilizes silver nanoparticles and borax and contains a scent is needed.

A composition of the present invention may be advantageously produced by a method of the present invention, as shown in FIG. 1. The methods disclosed herein may be used to prepare an odor reducing composition. In some embodiments, the method may be used to prepare a scented odor reducing composition. In an embodiment, a method of making a scented composition compromises heating deionized water in a first vessel, adding disodium tetraborate decahydrate (borax) to the deionized water, essentially dissolving the borax, adding a first stock mixture of silver nitrate to the composition, mixing the composition until the silver nitrate is essentially converted to silver nanoparticles within the composition, preparing a second stock mixture of scented essential oil and anhydrous ethanol, adding the second stock mixture to the composition, and mixing the composition until the composition is essentially an evenly distributed micro-emulsion. In some embodiments, the composition may be made in bulk and held for further processing.

In some embodiments, the deionized water may be heated to at least 40° C. The composition may not be stable at temperatures less than 40° C. Temperatures greater than 40° C. may not impact the stability of the composition. In other embodiments, the deionized water may be heated to between 40 to 60° C.

In certain embodiments, the method involves agitating the deionized water during the borax addition. In some embodiments, the dissolution of the borax may be analyzed visually by taking a sample of the composition and viewing it using a clear container. Undissolved borax crystals may be visible during the visual analysis, indicating that the borax may not be fully dissolved into the deionized water composition.

Once the borax is essentially dissolved, in some embodiments the method includes agitating the composition during the first stock mixture addition. In some embodiments, the first stock mixture may be prepared by dissolving silver nitrate in deionized water in a second vessel. The composition may be heated to above 40° C. to aid the conversion of the silver nitrate from the first stock mixture into silver nanoparticles. In certain embodiments, the conversion of the silver nitrate mixture to silver nanoparticles may be confirmed using a color-changing analysis under ultraviolet light. The analysis may yield a positive result for the conversion to silver nanoparticles when droplets of the composition develop darkened coloration on a paper at the location of the droplet without spreading to other areas of the analysis paper. In some embodiments, the silver nanoparticles may be dispersed such that a colloidal suspension may be formed with a separation distance of the nanoparticles of 10 to 100 nanometers.

In some embodiments, the mixing of the composition in the first vessel may be performed by stirring, shaking, agitating, and/or circulating the composition. Similarly, in other embodiments, the mixing in the second vessel may be performed by stirring, shaking, agitating, and/or circulating the mixture.

The present method may also comprise preparing a second stock mixture of scented essential oil and anhydrous ethanol, adding the second stock mixture to the composition, and mixing the composition until the composition is essentially an evenly distributed micro-emulsion. A homogeneous composition of the anhydrous ethanol and scented essential oil may be desirable. The scented essential oil may be effective at low concentration; therefore a maximum amount may be added in some embodiments.

In some embodiments, the composition with scented oil may be analyzed under magnification to verify the sufficient mixing for the formation of the micro-emulsion. In certain embodiments, the composition may be analyzed under at least 40× magnification to verify the formation of the micro-emulsion.

The method presented herein may be further comprised of a pre-cleaning step of the first vessel. In some embodiments, the first vessel may be cleaned with a heated anionic surfactant, such as a sodium lauryl sulfate mixture. For example, in some embodiments, a 1% by weight sodium lauryl sulfate and water composition may be heated to 70 to 80° C. to ensure the cleanliness of the first vessel prior to mixing the composition. Multiple rinses of the first vessel may be necessary after the sodium lauryl sulfate composition cleaning to ensure no surfactant remains.

To further ensure the cleanliness of the first vessel prior to mixing the odor reducing composition, an alkaline cleaner such as Enforce LP™ may be used to clean the first vessel in some embodiments. In certain embodiments, the alkaline cleaner may be sprayed on the surfaces of the first vessel and associated equipment and allowed to sit for a period of time of approximately 15 minutes prior to thoroughly rinsing to remove any residue.

In some embodiments, the pre-cleaning steps may include both the anionic surfactant and the alkaline cleaner. In other embodiments, the pre-cleaning steps may be followed by a series of deionized water rinses of the mixing vessels. In certain embodiments, the effectiveness of the pre-cleaning steps may include a visual and/or olfactory inspection.

Also described herein is an article of manufacture comprising a composition of about 0.0008 to 0.08 wt. % silver nanoparticles, 0.18 to 7 wt. % disodium tetraborate decahydrate (borax), up to 5 wt. % anhydrous ethanol, up to 0.2 wt. % scented essential oil, and the remainder deionized water. In some embodiments, the composition may be capable of being dispersed as a mist.

The composition presented herein may be used independently or in conjunction with other applications to minimize odors. In some embodiments designed for independent use, the composition may be evenly dispersed within the area to reduce or eliminate a particular odor. The dispersion may be accomplished by means comprising misting, swabbing, and/or soaking the target area. The target area may include, but is not limited to, furniture, carpet, animal beds, clothing, vehicle upholstery, and other textiles. The composition may have prolonged odor reducing effects due to the antimicrobial properties of the silver nanoparticles and the excess borax. The prolonged effect may not only eliminate existing odors, but also limit formation of new odors.

In other embodiments, the odor reducing composition may be used in conjunction with other products. These products include, but are not limited to, liquid soap, deodorant stick, shampoo, room deodorizing spray, and other products where antimicrobial and odor reducing properties would be desirable.

Example 1: Reference Composition

| Component | Amount |
|---|---|
| DiH$_2$O | 986.15 mL |
| Borax | 13.35 g |
| AgNO$_3$ | 0.0849 g |

An odor reducing composition may be prepared as follows. A pre-cleaning of the mix tank was performed. A 1% sodium lauryl sulfate (CH$_3$(CH$_2$)$_{10}$CH$_2$(OCH$_2$CH$_2$)$_n$OSO$_3$Na) solution in water at 70-80° C. was prepared. The mix tank was rinsed with the warm 1% sodium lauryl sulfate solution and then rinsed with hot water until all surfactant has been removed. A solution of Enforce LP™ (3 oz Enforce LP per gallon of water) was prepared, sprayed on the surfaces of the mix tank and associated equipment, and allowed to sit for approximately 15 minutes. The mix tank was thoroughly rinsed with hot water until all residue had been removed. A fill-rinse of the mix tank with deionized water was performed 3 times to remove all cleaning agents. The mix tank was inspected to ensure there were no visual contamination or residual smell within the tank.

A working stock of silver particles was prepared by dissolving 0.0849 g of silver nitrate (AgNO$_3$) (CAS No. 7761-88-8) in 5 mL of deionized water (DiH$_2$O) in a second vessel.

To prepare the composition, 986.15 mL of DiH$_2$O was added to the mix tank and heated to a temperature of 40° C. to 60° C. 13.35 g of disodium tetraborate decahydrate (Na$_2$B$_4$O$_7$.10H$_2$O, commonly known as Borax) (CAS No. 1303-96-4) was added to the mix tank under agitation. The mix tank was agitated until all the Borax was dissolved. A visual inspection of sample of the composition was performed using a clear container to ensure there were no undissolved Borax crystals. Once the Borax had essentially dissolved, the working stock of silver particles was added to the mix tank under agitation. The composition was agitated in the mix tank for 10 to 20 minutes, until the silver particles were essentially converted into silver nanoparticles within the composition.

To confirm the conversion of the silver nitrate mixture to silver nanoparticles within the composition, a sample was taken and a color-changing analysis was performed. The analysis yielded a positive result when 3 to 4 droplets of the composition were placed on a single location of a paper towel, exposed to ultraviolet light and a darkened coloration developed on the paper without spreading to the wetted area. The odor reducing composition was complete.

Example 2: New Composition

| Component | Amount |
|---|---|
| DiH$_2$O | 986.15 mL |
| Borax | 13.35 g |
| AgNO$_3$ | 0.0849 g |
| Ethanol, anhydrous | 1.28 oz |
| Scented essential oil | <0.064 oz (2-5 drops) |

An odor reducing composition may be prepared as follows. A pre-cleaning of the mix tank was performed. A 1% sodium lauryl sulfate (CH$_3$(CH$_2$)$_{10}$CH$_2$(OCH$_2$CH$_2$)$_n$OSO$_3$Na) solution in water at 70-80° C. was prepared. The mix tank was rinsed with the warm 1% sodium lauryl sulfate solution and then rinsed with hot water until all surfactant has been removed. A solution of Enforce LP™ (3 oz Enforce LP per gallon of water) was prepared, sprayed on the surfaces of the mix tank and associated equipment, and allowed to sit for approximately 15 minutes. The mix tank was thoroughly rinsed with hot water until all residue had been removed. A fill-rinse of the mix tank with deionized water was performed 3 times to remove all cleaning agents. The mix tank was inspected to ensure there were no visual contamination or residual smell within the tank.

A working stock of silver particles was prepared by dissolving 0.0849 g of silver nitrate (AgNO$_3$) (CAS No. 7761-88-8) in 5 mL of deionized water (DiH$_2$O) in a second vessel.

A working stock of scent solution was prepared by adding 1.28 oz of anhydrous ethanol (CH$_3$CH$_2$OH) (CAS No. 64-17-5) and 2-5 drops (no more than 0.064 oz) of Green Tea essential oil. The scent solution was mixed until the oil was totally dissolved in the ethanol and a homogenous solution was formed.

To prepare the composition, 986.15 mL of DiH$_2$O was added to the mix tank and heated to a temperature of 40° C. to 60° C. 13.35 g of disodium tetraborate decahydrate (Na$_2$B$_4$O$_7$.10H$_2$O, commonly known as Borax) (CAS No. 1303-96-4) was added to the mix tank under agitation. The mix tank was agitated until all the Borax was dissolved. A visual inspection of sample of the composition was performed using a clear container to ensure there were no undissolved Borax crystals. Once the Borax had essentially dissolved, the working stock of silver particles was added to the mix tank under agitation. The composition was agitated in the mix tank for 10 to 20 minutes, until the silver particles were essentially converted into silver nanoparticles within the composition.

To confirm the conversion of the silver nitrate mixture to silver nanoparticles, a sample was taken and a color-changing analysis was performed. The analysis yielded a positive result when 3 to 4 droplets of the composition were placed on a single location of a paper towel, exposed to ultraviolet light and a darkened coloration developed on the paper without spreading to the wetted area. The odor reducing solution was maintained at 40° C. to 60° C. for the addition of the scent solution.

The previously prepared scent stock solution was added to the odor reducing solution under agitation and agitated for 5 minutes. The resulting composition had a slightly hazy appearance and evidenced a micro-emulsion under 40× magnification. The scented odor reducing composition was complete.

The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individual recited herein. All methods described herein can be performed in any suitable order unless otherwise indicated or clearly contradicted by context.

Various embodiments of the invention have been described herein. It should be recognized that these embodiments are merely illustrative of the present invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated or otherwise clearly contradicted by context.

What is claimed is:

1. A scented odor reducing composition comprising about 0.0008 to 0.08 wt. % silver nanoparticles;
0.18 to 7 wt. % disodium tetraborate decahydrate;
up to 0.2 wt. % scented essential oil; and
deionized water.

2. The composition of claim 1, comprising about 0.005 to 0.01 wt. % silver nanoparticles; and
0.5 to 2 wt. % disodium tetraborate decahydrate.

3. The composition of claim 1, wherein the composition has a pH greater than 8.

4. The composition of claim 3, wherein the composition has a pH between 9 and 10.

5. The composition of claim 1, wherein the composition comprises a colloidal suspension and the silver nanoparticles are dispersed in the colloidal suspension.

6. The composition of claim 5, wherein the silver nanoparticles in the colloidal suspension have a separation distance of about 10 to about 100 nanometers.

7. The composition of claim 1, wherein the scented essential oil is capable of forming a micro-emulsion in the composition.

8. The composition of claim 1, wherein the composition is capable of forming a mist.

9. The composition of claim 1, wherein the scented essential oil is hydrophobic.

10. The composition of claim 1, wherein the silver nanoparticles comprise uncomplexed elemental silver.

11. A method of making an odor reducing composition of claim 1 comprising:
washing a vessel with a first solution comprising 1% sodium lauryl sulfate;
adding deionized water to the washed vessel;
heating deionized water in the vessel;
adding disodium tetraborate decahydrate;
adding a second solution comprising silver nitrate;
adding a third solution comprising a scented essential oil and an anhydrous ethanol; and
mixing the composition until the composition is an essentially evenly distributed micro-emulsion.

12. The method of claim 11, further comprising mixing the composition until the silver nitrate is essentially converted to silver nanoparticles within the composition.

13. The method of claim 12, further comprising dispersing the silver nanoparticles to form a colloidal suspension with a separation distance of the nanoparticles of about 10 to about 100 nanometers.

14. The method of claim 11, further comprising rinsing the first vessel with a chlorinated alkaline detergent.

15. A method for using the composition of claim 1 to minimize an odor comprising introducing the composition to an environment by spraying or applying to a surface.

16. The method of claim 15, wherein the composition is applied to a surface, wherein said surface comprises a living being or article of manufacture.

17. The method of claim 16, wherein the living being comprises a portion of a human or an animal.

18. The method of claim 16, wherein article of manufacture comprises at least one of an animal bed, vehicle upholstery, or hunting textiles.

19. The method of claim 15, wherein the odor reducing composition may be used in conjunction with at least one of a liquid soap, a deodorant stick, a shampoo, or a room deodorizing spray.

* * * * *